United States Patent [19]
Volk

[11] Patent Number: 5,757,464
[45] Date of Patent: May 26, 1998

[54] INDIRECT OPHTHALMOSCOPY CONTACT LENS DEVICE WITH COMPOUND CONTACT LENS ELEMENT

[75] Inventor: Donald A. Volk, Mentor, Ohio

[73] Assignee: Volk Optical, Inc., Mentor, Ohio

[21] Appl. No.: 705,526

[22] Filed: Aug. 29, 1996

[51] Int. Cl.[6] ........................................ A61B 3/00
[52] U.S. Cl. ................................ 351/219; 351/205
[58] Field of Search .................... 351/205, 219, 351/247, 159, 160 R; 359/708, 712

[56] References Cited

U.S. PATENT DOCUMENTS

| | | | |
|---|---|---|---|
| 4,502,764 | 3/1985 | Riquin | 351/219 |
| 5,309,187 | 5/1994 | Crossman et al. | 351/219 |
| 5,430,506 | 7/1995 | Volk | 351/205 |
| 5,436,680 | 7/1995 | Volk | 351/219 |
| 5,479,222 | 12/1995 | Volk | 351/219 |
| 5,523,810 | 6/1996 | Volk | 351/219 |
| 5,526,189 | 6/1996 | Heacock et al. | 351/205 |

*Primary Examiner*—Huy Mai
*Attorney, Agent, or Firm*—Spencer & Frank

[57] ABSTRACT

An indirect, contact ophthalmoscopy lens device for use with a slit lamp or other biomicroscope comprises a compound contact lens element and an image forming lens system. The compound contact lens element includes a posterior lens portion having a concave posterior surface with a curvature corresponding to a curvature of an average cornea and anterior lens portion having a convex anterior surface. A middle lens portion is disposed between the posterior and anterior lens portions and has an index of refraction that is different from the index of refraction of air and is different from the index of refraction of each of the posterior and anterior lens portions. The middle lens portion includes a posterior surface that conforms with intimate contact to the anterior surface of the posterior lens portion and an anterior surface that conforms with intimate contact to the posterior surface of the anterior lens portion. In one embodiment the image forming lens system is disposed anterior of the compound contact lens element for capturing light exiting a patient's eye and refracted by the compound contact lens element for forming a real image of the patient's fundus outside the patient's eye. In another embodiment, a compound lens constituting a complete imaging system includes a posterior lens portion that contacts the eye, an anterior lens portion that comprises the image forming lens and a middle lens portion that conforms with intimate contact to the posterior and anterior lens portions.

18 Claims, 3 Drawing Sheets

1

INDIRECT OPHTHALMOSCOPY CONTACT LENS DEVICE WITH COMPOUND CONTACT LENS ELEMENT

BACKGROUND OF THE INVENTION

The invention relates to an indirect ophthalmoscopy contact lens device for observing and treating the fundus of a patient's eye in conjunction with a slit lamp biomicroscope as well as for use in vitreoretinal surgery in conjunction with an operating microscope. Such a device includes a contact lens element and an image forming lens system mounted in a housing, with the image forming lens system being anterior of the contact lens element. The contact lens element has a concave posterior surface with a profile substantially corresponding to the shape of the average cornea for placement on the patient's eye. Light emanating from the patient's retina which passes through the contact lens element is refracted by the image forming lens system to form an aerial image of the patient's fundus anterior of the image forming lens.

An ophthalmoscopic contact lens device of this type is disclosed, for example, in my prior U.S. patent application Ser. No. 08/465,461, filed Jun. 5, 1995, now U.S. Pat. No. 5,523,810. That device includes a compound contact lens element that has two components that are optically cemented together at substantially matching surfaces. More specifically, the compound contact lens element of my prior invention includes a posterior lens portion and an anterior lens portion. The posterior lens portion has a concave posterior surface that has a curvature substantially corresponding to the curvature of the average cornea for placement on a patient's eye and an anterior surface that is fastened by an optical glue or cement to the substantially matching posterior surface of the anterior lens portion which additionally has a convex anterior surface. The posterior and anterior lens portions of the contact lens element have different optical properties, for example different indices of refraction, or different Abbe values, for bending light exiting the patient's eye so that the light is collected by the image forming lens system for creating an image of the patient's fundus outside the eye.

The optical cement that fixes the surfaces of the compound contact lens element in my prior invention comprises a relatively thin layer that has an index of refraction, and therefore light bending properties, corresponding to that of one of the lens portions. Since the optical cement is a necessary component of the compound contact lens element as described in my prior application, it would be beneficial if the optical cement could be employed in a useful manner to independently assist in refracting the light to improve the overall optical performance of the device. This in effect provides a compound contact lens comprised of three lens portions. As described below, I have discovered that the middle lens portion may be comprised solely of optical cement, various combination of optical cement, glass and/or plastic, or a liquid optical media.

SUMMARY OF THE INVENTION

It is therefore an object of the invention to provide an indirect, contact ophthalmoscopy lens device that has a compound contact lens element with improved optical qualities including an increased field of view compared to known devices.

The above and other objects are accomplished in accordance with one embodiment of the invention by the provision of an indirect, contact ophthalmoscopy lens device, comprising: a compound contact lens element including a posterior lens portion having a first index of refraction and including a concave posterior surface with a curvature corresponding to a curvature of an average cornea and an anterior surface, an anterior lens portion having a second index of refraction and including a convex anterior surface and a posterior surface, and a middle lens portion disposed between the posterior and anterior lens portions and having a third index of refraction that is different from air and different from the first and second indices of refraction, the middle lens portion including a posterior surface that conforms with intimate contact to the anterior surface of the posterior lens portion and an anterior surface that conforms with intimate contact to the posterior surface of the anterior lens portion; and an image forming lens system disposed anterior of the compound contact lens element for capturing light exiting a patient's eye and refracted by the compound contact lens element for forming a real image of the patient's fundus outside the patient's eye.

The indirect contact ophthalmoscopy lens device of the invention may provide a very large field of view, up to and beyond 160°, and according to one embodiment follows the design concept of an aplanat lens system which satisfies the Abbe sine condition by providing a series of refracting surfaces having a descending curvature that corrects for spherical aberration and coma.

According to one aspect of the invention, the middle lens portion has an index of refraction greater than the index of refraction of air (i.e. greater that 1). According to another aspect of the invention, the index of refraction of the middle lens portion is greater than the index of refraction of the posterior lens portion. According to yet another aspect of the invention the anterior lens portion has an index of refraction that is greater than the index of refraction of the middle lens portion.

According to one embodiment of the invention, the middle lens portion comprises optical cement. In a preferred form of this embodiment the middle lens is comprised solely of optical cement. However, the middle lens portion could conceivably additionally include other optical material, for example, glass or plastic, cemented between the posterior and anterior lens portion.

According to another embodiment, the middle lens portion comprises a liquid optical media. The liquid optical media will have an index of refraction greater than air and additionally will have an index of refraction greater or lesser than the index of refraction of both the posterior and anterior lens portions.

According to a further embodiment of the invention, the compound contact lens element comprises a complete imaging system, wherein the anterior lens of the compound contact lens element comprises the imaging lens, so that no additional imaging lens separate from the compound contact lens element is required.

DETAILED DESCRIPTION OF THE PREFERRED EMBODIMENT

Figure 1:
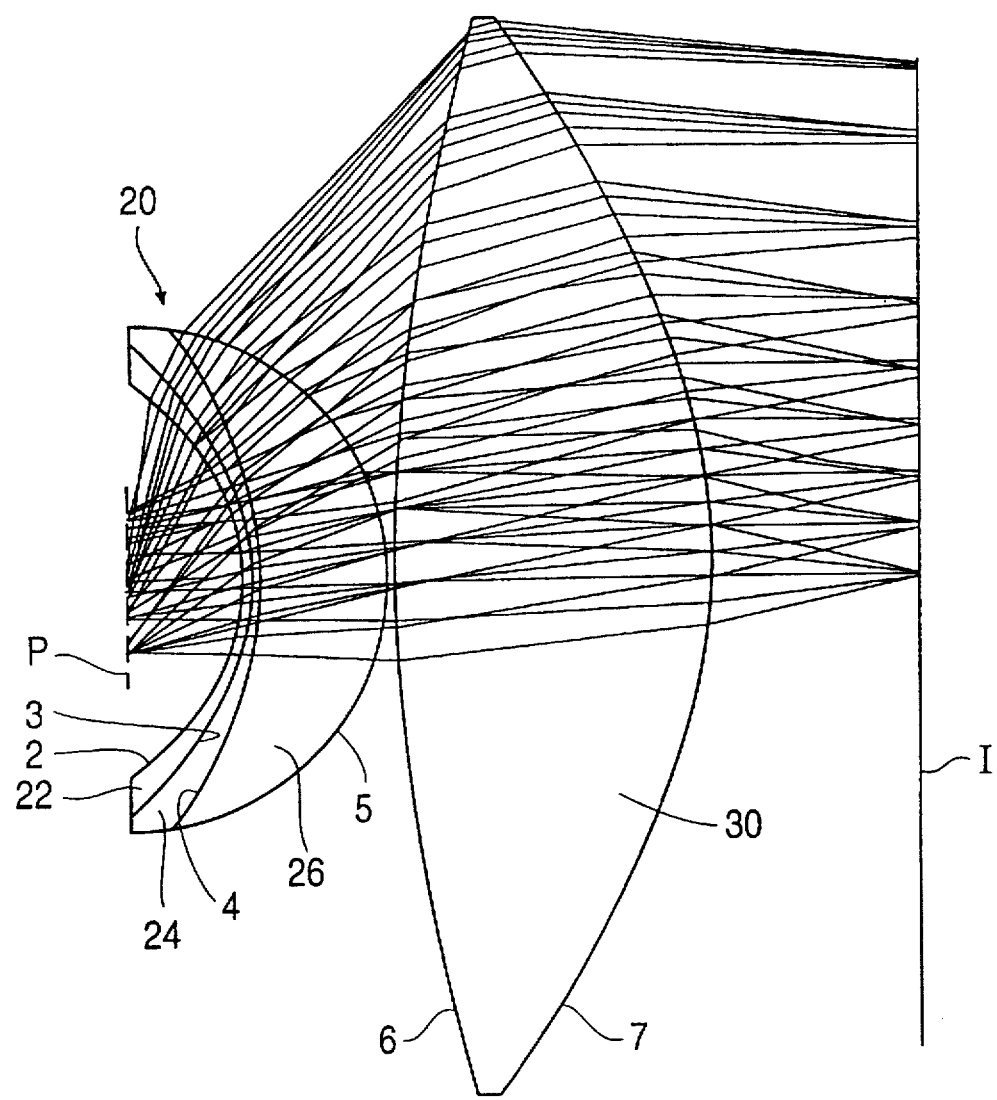
FIG. 1 shows a lens layout of one embodiment of an indirect, contact ophthalmoscopy lens device according to the invention with an overlaid ray tracing.

FIG. 1 shows a lens layout of an indirect, contact ophthalmoscopy lens device according to one embodiment of the invention that includes a compound contact lens element 20 and an image forming lens system comprising in this instance a single biconvex lens 30. In practice, compound contact lens element 20 and image forming lens 30 may be fixed relative to one another in a common cone shaped frame or housing (not shown) as known in the art, or alternatively, compound contact lens element 20 and image forming lens system 30 may be separately mounted in ring frames and adjusted separately in relation to the eye as discussed below.

Compound contact lens element 20 includes three components, namely a posterior lens portion 22, a middle lens portion 24, and anterior lens portion 26. Posterior lens portion 22 has a concave posterior surface 2 that has a curvature corresponding to the curvature of an average cornea for placement in contact with a patient's eye. Posterior lens portion 22 has a convex anterior surface 3 which is less steeply curved than concave posterior surface 2.

Anterior lens portion 26 has a concave posterior surface 4 and a convex anterior surface 5. Concave posterior surface 4 of anterior lens portion 26 is less steeply curved than convex anterior surface 3 of posterior lens portion 22.

Middle lens portion 24 comprises a transparent optical material, in this example, consisting entirely of an optical cement which, when set, forms a posterior surface that conforms with intimate contact to the surface and shape of anterior surface 3 of posterior lens portion 22 and an anterior surface that conforms with intimate contact to the surface and shape of posterior surface 4 of anterior lens portion 26. Further, the optical cement comprising middle lens 24 has an index of refraction that is different from air as well as different from the index of refraction of posterior lens portion 22 and anterior lens portion 26, so that light passing through the compound lens is refracted at the interface of the posterior and middle lens portions and at the interface of the middle and anterior lens portions.

According to one example of the device shown in FIG. 1, posterior lens portion 22 comprises PMMA acrylic having an index of refraction of 1.491. The optical cement of middle lens portion 24 comprises NOA G1 made by Norland Products, Inc., having an index of refraction of 1.56, and anterior lens portion 26 comprises LAH58 Lanthanum glass manufactured by O'Hara Corporation having an index of refraction of 1.883. Image forming lens 30 may be made, for example, of LAL59 glass also manufactured by O'Hara Corporation having an index of refraction of 1.734, and preferably having a posterior surface 6 that is less steeply curved than its anterior surface 7.

The following Table I summarizes the characteristics of the lens surfaces and their relative spacing in the aforementioned example. The Radius in the table is the apical radius of curvature and is either positive or negative, depending on whether the surface is convex or concave, respectively. The Distance is the distance of the surface from the corneal apex. A Conic Constant of 0 indicates a spherical surface and a negative conic constant indicates an aspheric conoid. The Diameter is the distance between the outer edges of the respective lens.

TABLE I

| Surface | Radius (mm) | Conic Constant | Distance from Corneal Apex (mm) | Diameter (mm) |
| --- | --- | --- | --- | --- |
| 2 | −7.55 | −0.18 | 0.00 | 12 |
| 3 | 9.50 | 0 | 0.25 | 15 |

TABLE I-continued

| Surface | Radius (mm) | Conic Constant | Distance from Corneal Apex (mm) | Diameter (mm) |
| --- | --- | --- | --- | --- |
| 4 | −12.68 | 0 | 0.50 | 15 |
| 5 | 7.35 | 0 | 4.20 | 15 |
| 6 | 35.00 | −7.00 | 4.45 | 30 |
| 7 | 13.5 | −2.00 | 14.45 | 30 |

In use, the compound contact lens element 20 of the indirect ophthalmoscopy lens device constructed as described above is placed on a patient's cornea. Image forming lens system 30 may be mounted in the same frame (not shown) as the compound contact lens element or may be mounted in a separate frame and held or maintained in position anterior of the compound contact lens element as shown in FIG. 1.

Light rays which originate at the patient's retina (not shown) pass through the pupil, exit the eye and pass through the lens device in accordance with the partial ray tracing which overlays the lens layout in FIG. 1. Although the ray tracing shows light proceeding as parallel bundles from a pupil location in air, the ray tracing through the lens device follows similar pathways as do light rays which originate at the retina and proceed through the vitreous humor, crystalline lens, aqueous humor and cornea of the eye to the various lens elements of the device. The use of parallel bundles in air is a simplified representation of the optical system of the emmetropic human eye. The pupil location in air is represented in FIG. 1 as line P.

As illustrated, light rays exiting the eye are successively refracted toward the optical axis at the respective surfaces 2, 3, 4 and 5 of the compound contact lens element 20 and are collected by image forming lens system 30 which focuses the rays in an image plane I where a real image of the patient's retina is formed. In the above example, the real image is created at a location 5.89 mm anterior of the anterior surface of image forming lens 30.

Further, because the cement bonding the posterior and anterior lens portions together functions, in the described example, as a middle lens, the described compound contact lens element actually comprises three lens portions, presenting two internal interfaces at which light passing through the lens is refracted, as opposed to only one internal interface presented by a compound lens having only two lens portions as disclosed in my prior patent application. The additional bending of the light due to the additional interface allows the image forming lens to collect far peripheral light rays, thus providing a wide field of view of the eye fundus. An ophthalmoscopy lens device constructed in accordance with the present invention provides a very large field of view, approximately 158° to 160°, with correction for spherical aberration and coma.

As noted previously, the middle lens portion may be comprised solely of optical cement, or, may include other optical material, for example, glass or plastic, cemented between the posterior and anterior lens portions. Alternatively, the middle lens portion may comprise a liquid optical media encapsulated between the posterior and anterior lens portions as shown in FIG. 2.

Figure 2:
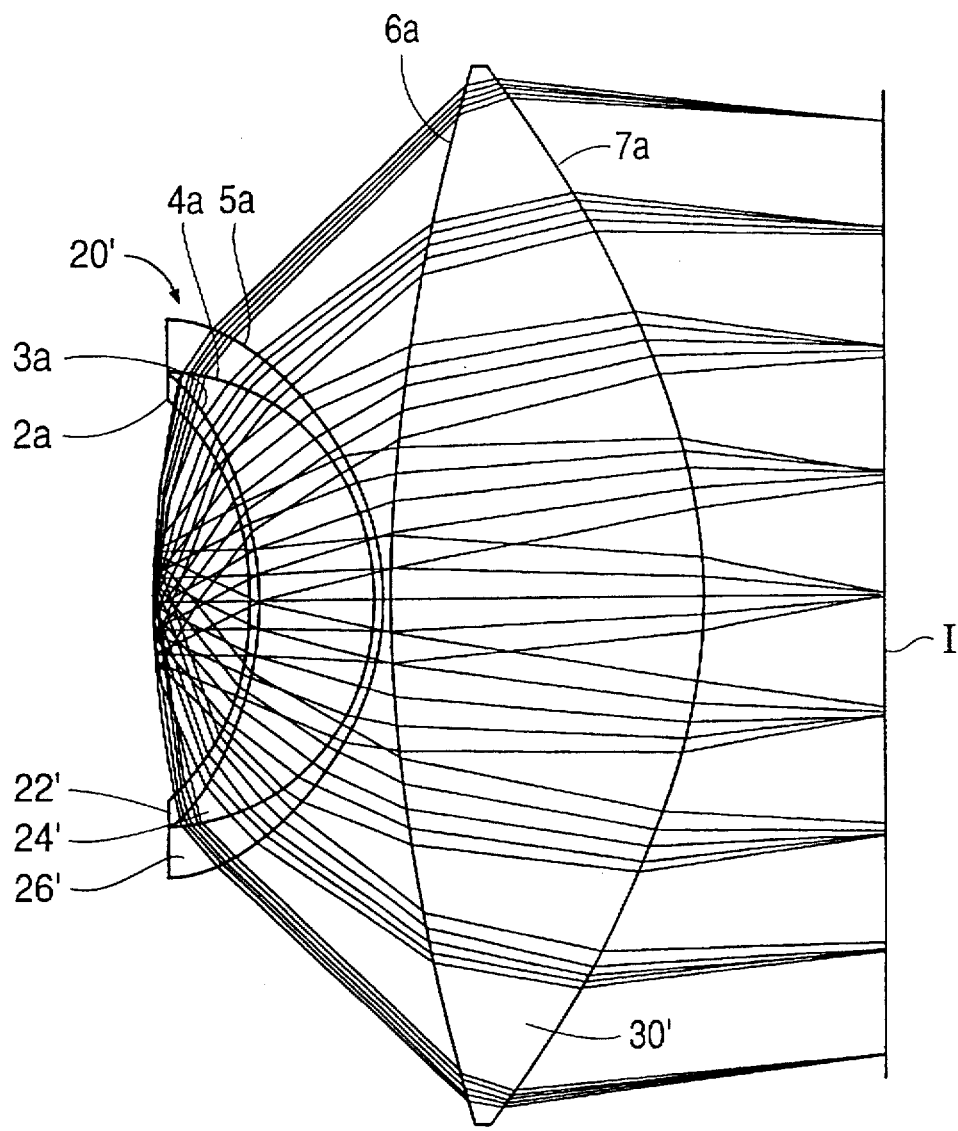
FIG. 2 shows a lens layout of another embodiment of the indirect, contact ophthalmoscopy lens device according to the invention, again with an overlaid ray tracing.

The lenses and lens portions in FIG. 2 corresponding to like lenses and lens portions in FIG. 1 are identified by corresponding reference numerals followed by a prime (') and lens surfaces in FIG. 2 corresponding to like surfaces in FIG. 1 are identified by corresponding reference numerals followed by the letter "a".

According to one example implementing the embodiment of FIG. 2, the liquid optical media of middle lens portion 24' comprises an EH series refractive index liquid manufactured by R. P. Cargille Laboratories, Inc. having an index of refraction of 2.11. The liquid optical media is encapsulated between posterior lens portion 22' and anterior lens portion 26', both of which may have optical power. An aspheric curvature may be utilized on at least one of the surfaces for corrective purposes. In this example, at least anterior surface 5a of anterior lens portion 26' is aspheric. Also in this example, both posterior lens portion 22' and anterior lens portion 26' are made of PMMA acrylic having an index of refraction of 1.491. Image forming lens 30' is made of LAL59 glass having an index of refraction of 1.734. Table II below summarizes the characteristics of the lens surfaces and their relative spacing in this example. The column headings have the same meaning as discussed in connection with Table I above.

TABLE II

| Surface | Radius (mm) | Conic Constant | Distance from Corneal Apex (mm) | Diameter (mm) |
| --- | --- | --- | --- | --- |
| 2a | −7.55 | −0.18 | 0.00 | 11.7 |
| 3a | 9.50 | 0 | 0.25 | 13.6 |
| 4a | −6.57 | 0 | 4.95 | 13.6 |
| 5a | 7.70 | −0.15 | 5.20 | 16 |
| 6a | 35.00 | −7.00 | 5.45 | 30 |
| 7a | 13.5 | −2.13 | 14.45 | 30 |

FIG. 2 depicts the path of light rays emanating from an emmetropic eye and passing through a device constructed according to the above described exemplary implementation of the FIG. 2 embodiment. When a lens constructed according to this example is placed on an emmetropic eye, a real image of the fundus is created in a plane spaced 4.67 mm from anterior surface 7a of image forming lens 30' in a manner similar to that discussed in connection with FIG. 1.

Figure 3:
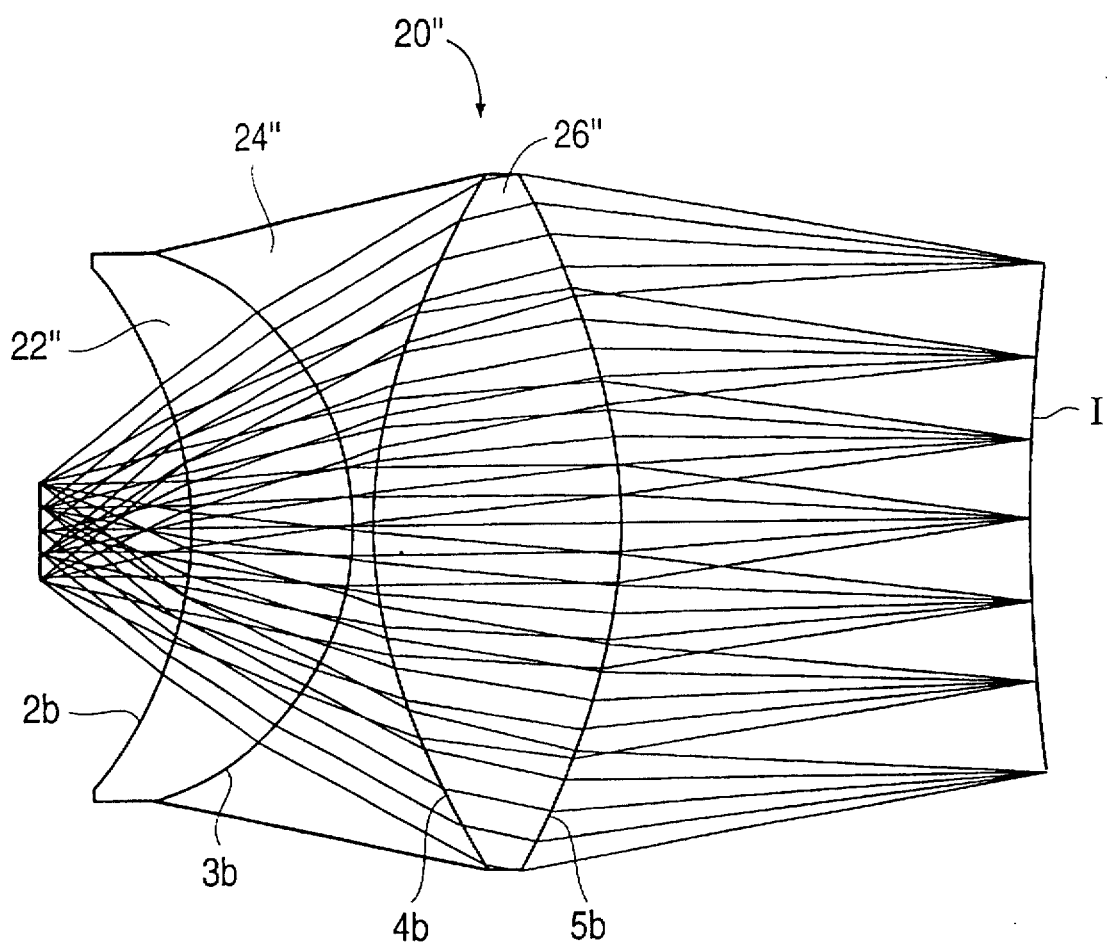
FIG. 3 shows a lens layout of another embodiment of the indirect, contact ophthalmoscopy lens device according to the invention, again with an overlaid ray tracing.

FIG. 3 shows an embodiment of the invention in which the 3-part compound contact lens element functions as the complete imaging system, without an additional image forming element as in the prior two embodiments. The components in FIG. 3 corresponding to like components in FIG. 1 are identified by corresponding reference numerals followed by a double prime (") and lens surfaces in FIG. 3 corresponding to like surfaces in FIG. 1 are identified by corresponding reference numerals followed by the letter "b".

Thus, FIG. 3 shows a compound lens element 20" which includes a posterior lens portion 22", a middle lens portion 24" and an anterior lens portion 26". Posterior lens portion 22" has a concave posterior surface 2b that has a curvature corresponding to the curvature of an average cornea for placement in contact with a patient's eye. Posterior lens portion 22" has a convex anterior surface 3b. Anterior lens portion 26" has a convex posterior surface 4b and a convex anterior surface 5b. Middle lens portion 24" comprises a transparent optical material which may be composed of an optical epoxy, polyurethane polymer, CR-39 polymer, acrylic polymer, acrylate polymer or other suitable polymer which is cemented with intimate contact to the inner convex surfaces 3b and 4b, respectively, of the posterior and anterior lens portions 22" and 26". Alternatively middle lens portion 24" may be composed entirely of optically clear cement including various optical epoxies, acrylate polymers or other clear plastics, or middle lens portion 24" may be liquid filled in a manner similar to that described in connection with the embodiment shown in FIG. 2. In each instance, middle lens portion 24" has a posterior surface that conforms with intimate contact to the surface and shape of anterior surface 3b of posterior lens portion 22" and an anterior surface that conforms with intimate contact to the surface and shape of posterior surface 4b of anterior lens portion 26". In this embodiment, the two outer lens portions, that is posterior lens portion 22' and anterior lens portion 26", have relatively high indices of refraction compared to the index of refraction of middle lens portion 24". In an exemplary implementation of the embodiment of FIG. 3, the two outer lens portions, 22" and 26", are made of LAH58 glass having an index of refraction of 1.883 and middle lens portion 24" is made of PMMA acrylic with an index of refraction of 1.491.

Table III below summarizes the characteristics of the lens surfaces and their relative spacing according to this example. The column headings have the same meaning as discussed in connection with Table I and II above. Posterior lens portion 22' has a diameter of 11.50 mm which makes it suitable for use in vitreoretinal surgery.

TABLE III

| Surface | Radius (mm) | Conic Constant | Distance from Corneal Apex (mm) | Diameter (mm) |
| --- | --- | --- | --- | --- |
| 2b | −7.7 | 0 | 0.00 | 11.00 |
| 3b | 5.7 | 0 | 3.5 | 11.50 |
| 4b | 8.3 | −1.93724 | 4.00 | 14.00 |
| 5b | 8.9 | −2.28734 | 9.5 | 14.00 |

FIG. 3 depicts the path of light rays emanating from an emmetropic eye and passing through a device constructed according to the above described exemplary implementation of the FIG. 3 embodiment. In this embodiment, anterior lens portion 26" itself functions as the imaging forming lens, so that the compound lens 20" constitutes the complete imaging system, without a separate image forming lens. When a lens constructed according to this example is placed on an emmetropic eye, a real image of the fundus is created in air anterior to lens portion 26" in a slightly curved image plane I as shown.

The invention has been described in detail with respect to a preferred embodiment, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. An indirect, contact ophthalmoscopy lens device for use with a slit lamp or other biomicroscope, comprising:

a compound contact lens element including a posterior lens portion having a first index of refraction and including a concave posterior surface with a curvature corresponding to a curvature of an average cornea and an anterior surface, an anterior lens portion having a second index of refraction and including a convex anterior surface and a posterior surface, and a middle lens portion disposed between the posterior and anterior lens portions and having a third index of refraction that is different from air and different from the first and second indices of refraction, the middle lens portion including a posterior surface that conforms with intimate contact to the anterior surface of the posterior lens portion and an anterior surface that conforms with intimate contact to the posterior surface of the anterior lens portion; and an image forming lens system disposed anterior of the compound contact lens element for capturing light exiting a patient's eye and refracted by the compound contact lens element for forming a real image of the patient's fundus outside the patient's eye.

2. The device according to claim 1, wherein the third index of refraction of the middle lens portion is greater than the index of refraction of air.

3. The device according to claim 1, wherein the first index of refraction of the posterior lens portion is less than the third index of refraction of the middle lens portion.

4. The device according to claim 1, wherein the first index of refraction of the posterior lens portion is greater than the third index of refraction of the middle lens portion.

5. The device according to claim 3, wherein the second index of refraction of the anterior lens portion is greater than the third index of refraction of the middle lens portion.

6. The device according to claim 1, wherein the anterior surface of the posterior lens portion is convex and has a curvature that is less steep than the posterior surface of the posterior lens portion, and the posterior surface of the anterior lens portion is concave and has a curvature that is less steep than the convex anterior surface of the posterior lens portion.

7. The device according to claim 1, wherein the image forming lens system comprises a single biconvex lens having a posterior surface and an anterior surface, the posterior surface of the biconvex lens having a curvature that is less steep than the curvature of the anterior surface of the biconvex lens.

8. The device according to claim 1, wherein the middle lens portion comprises optical cement.

9. The device according to claim 1, wherein the middle lens portion is comprised solely of optical cement.

10. The device according to claim 1, wherein the middle lens portion comprises a liquid optical media encapsulated between the posterior and anterior lens portions.

11. The device according to claim 1, wherein the anterior surface of the posterior lens portion is convex and the posterior surface of the anterior lens portion is concave and has a curvature that is different from the curvature of the convex anterior surface of the posterior lens portion.

12. An indirect, contact ophthalmoscopy lens device for use with a slit lamp or other biomicroscope, comprising:

a compound lens including a posterior lens portion having a first index of refraction and including a concave posterior surface with a curvature corresponding to a curvature of an average cornea and an anterior surface, an anterior lens portion having a second index of refraction and including a convex anterior surface and a posterior surface, and a middle lens portion disposed between the posterior and anterior lens portions and having a third index of refraction that is different from air and different from the first and second indices of refraction, the middle lens portion including a posterior surface that conforms with intimate contact to the anterior surface of the posterior lens portion and an anterior surface that conforms with intimate contact to the posterior surface of the anterior lens portion, wherein the compound lens constitutes a complete imaging system for capturing light exiting a patient's eye and refracting the light for forming a real image of the patient's fundus outside the patient's eye.

13. The device according to claim 12, wherein the anterior surface of the posterior lens portion is convex and the posterior surface of the anterior lens portion is convex.

14. The device according to claim 12, wherein the middle lens portion comprises optical cement.

15. The device according to claim 12, wherein the middle lens portion comprises a clear plastic.

16. The device according to claim 12, wherein the middle lens portion comprises one of an optical epoxy, polyurethane polymer, CR-39 polymer, acrylic polymer and acrylate polymer.

17. The device according to claim 12, wherein the middle lens comprises an encapsulated liquid.

18. The device according to claim 12, wherein the third index of refraction of the middle lens portion is less than each of the first and second indices of refraction of the posterior and anterior lens portions, respectively.

* * * * *